United States Patent [19]

Magee, Jr.

[11] E Re. 30,284

[45] Reissued May 27, 1980

[54] POLYMERIC ALKOXYSILANES

[75] Inventor: Walter L. Magee, Jr., Danbury, Conn.

[73] Assignee: Stauffer Chemical Company, Westport, Conn.

[21] Appl. No.: 899,683

[22] Filed: Apr. 24, 1978

Related U.S. Patent Documents

Reissue of:

[64] Patent No.: 4,042,612
Issued: Aug. 16, 1977
Appl. No.: 756,310
Filed: Jan. 3, 1977

[51] Int. Cl.[2] ..... C07F 7/18

[52] U.S. Cl. ..... 556/428; 106/38.2; 106/55

[58] Field of Search ..... 260/448.8 R

[56] References Cited

U.S. PATENT DOCUMENTS

| | | | |
|---|---|---|---|
| 3,872,146 | 3/1975 | Rossmy | 260/448.8 R X |
| 3,948,963 | 4/1976 | Rossmy | 260/448.8 R X |

*Primary Examiner*—Paul F. Shaver

*Attorney, Agent, or Firm*—William C. Gerstenzang

[57] ABSTRACT

Polymeric alkoxysilanes which comprise a polymer network of the average formula $$Si(OR)_a(O-\overset{\overset{O}{\|}}{\underset{\underset{O}{\|}}{S}}-R^1)_bO_{\frac{4-a-b}{2}}$$

wherein each R is an independently selected hydrocarbon or hydrocarbon ether radical, each [R′]$R^1$ is an independently selected hydrocarbon radical, all of said radicals being free of aliphatic unsaturation, a has a value from 1 to 3; and b has a value from 0.0001 to 1.0. These polymers are made by reacting an alkoxysilane of the formula $$Si(OR)_aO_{\frac{4-a}{2}}$$

with water and with an organosulfonic acid of the formula $R^1SO_3H$. These polymers are useful in zinc-rich paints and in binders for investment castings.

6 Claims, No Drawings

POLYMERIC ALKOXYSILANES

Matter enclosed in heavy brackets [ ] appears in the original patent but forms no part of this reissue specification; matter printed in italics indicates the additions made by reissue.

BACKGROUND OF THE INVENTION

This invention relates to polymeric alkoxysilanes which are useful as binders for investment castings and zinc-rich paints, and to a process for making such polymeric alkoxysilanes.

Various organopolysiloxanes have been described in the prior art. These materials are generally prepared by partial hydrolysis of silicates or orthosilicates, and function as binders by curing in the presence of atmospheric moisture. However these products are subject to several disadvantages when used in commercial applications. For example, the presence of residual hydroxyl functionality in the polymer causes premature gellation even in the absence of moisture. Thus, the products must be sold with gel-time specifications, indicating the shelflife of the product, which is generally about 1 year.

Attempts have been made to introduce various organic moieties into these materials. Typical are the polymercaptoorgano and polyhydroxyorgano silanes and siloxanes described in U.S. Pat. No. 3,388,144 to M. C. Musolf et al and the organopolysiloxane having terminal acyloxy groups disclosed in U.S. Pat. No. 3,595,885 to G. Rossmy et al. However, the resulting siloxanes are not solvent-resistant, limiting their applications to [area] *areas* where this property is not required.

Other efforts have been directed to preparing organo polysiloxanes which are stable under certain conditions but have limited applications. For example, in U.S. Pat. No. 3,804,639 to Trulsson et al. it was proposed that a tetraalkyl or tetraalkoxyalkyl orthosilicate be condensed in a hydroxylic solvent, e.g., a lower alkanol or a monoalkyl ether of a glycol in the presence of a peroxide and a catalytic amount of a suitable strong organic acid, e.g., p-toluenesulfonic acid. The reaction caused the exchange of the alkoxy groups of the hydroxylic solvent for one or more of the alkoxy groups of the orthosilicate reagents. The ultimate product could be cured in the complete absence of moisture. However, these compositions, when cured, do not have a sufficient $SiO_2$ content to render them useful for investment casting where a high inorganic content is essential. Furthermore, the use of organic solvents and peroxides presents safety problems, in the formulation, storage and use of the resultant binder.

Still another approach described in the art involved introducing sulfate groups into organosiloxanes. For example, polysiloxane mixtures with terminal sulfuric acid groups are described in U.S. Pat. No. 3,655,712 to G. Rossmy. The mixtures are prepared by reacting certain organopolysiloxanes with $H_2S_2O_7$ or sulfuric acid, or by reacting organo-halopolysiloxanes with sulfuric acid. The presence of the terminal sulfuric acid groups does not stabilize the mixture towards premature gellation, since hydroxyl groups are present. Furthermore, the mixtures are derived from organosilicones making them unsuitable for casting applications where the solubility of the binding resin is important.

Another example of sulfonated organosilicon compounds is described in U.S. Pat. No. 3,187,033 to S. Nitzsche et al. The silane and organosiloxane starting materials are sulfonated to carbon atoms and not silicon atoms, resulting in materials that are hydrolytically stable and impervious to curing.

SUMMARY OF THE INVENTION

Now it has been found in accordance with this invention that polymeric alkoxysilanes that cure when exposed to moisture but are storage-stable can be obtained by introducing alkylsulfonic or arylsulfonic moieties into the polymer. Furthermore, the polymers contain alkoxy and/or aryloxysilyl groups, rendering them capable of converting to silica upon firing.

DESCRIPTION OF THE INVENTION

More in detail, the polymeric alkoxysilanes of this invention have the average general formula $$Si(OR)_a\left(O-\overset{\overset{O}{\|}}{\underset{\underset{O}{\|}}{S}}-R^1\right)_b O_{\frac{4-a-b}{2}} \qquad \text{I}$$

where each R is an independently selected hydrocarbon or hydrocarbon ether radical, each [R'] $R^1$ is an independently selected hydrocarbon radical, all of said radicals being free of aliphatic unsaturation, a is an integer from 1 to 3 and b is an integer from 0.0001 to 1.0.

The polymeric alkoxysilanes having the average general formula I are preferably prepared by reacting an alkoxysilane with an organo-sulfonic acid and water.

Suitable alkoxysilanes for use in the present invention have the general formula $$Si(OR)_a O_{\frac{4-a}{2}} \qquad \text{II}$$

where R and a are as previously described. Exemplary R groups are alkyl, cycloalkyl, aryl, alkaryl, aralkyl and alkoxyalkyl. Specific examples of these groups include methyl, isopropyl, butyl, dodecyl, octadecyl, cyclopentyl, cyclohexyl, phenyl, xylyl, mesityl, ethylphenyl, benzyl, phenylethyl, tolyl, naphthyl, methoxethyl, ethoxyethyl, octadecyloxymethyl etc. Compounds where R is an alkyl or an alkoxyalkylgroup of 1 to 18 carbon atoms, aryl or alkyl-substituted aryl, where the aryl has 6 to 13 ring carbon atoms and the alkyl substituent has 1 to 5 carbon atoms, are preferred.

Exemplary organo-sulfonic acids are those having the formula $$R^1SO_3H \qquad \text{III}$$

where $R^1$ is as previously described. Exemplary $R^1$ groups include those previously mentioned for R with the exception of alkoxyalkyl. Preferably $R^1$ is an alkyl of 1 to 18 carbon atoms, aryl or alkylsubstituted aryl where the aryl has 6 to 13 ring carbon atoms and the alkyl substituent has 1 to 5 carbon atoms. Exemplary acids include methanesulfonic acid, octadecylsulfonic acid, benzenesulfonic acid, p-toluenesulfonic acid, naphthylsulfonic acid and cresylsulfonic acid.

The molar ratio of alkoxysilane II to water, which are the two reactants which are present in major amounts, depends upon the particular alkoxysilane II starting material. For example, if partially hydrolyzed prepolymers are employed less water is required. Generally enough water is employed to provide from about 30% to about 80% hydrolysis of the alkoxysilane II. Thus, the molar ratio of alkoxysilane II to water can range anywhere from about 1:0.3 to about 1:1.5 and preferably from about 1:0.5 to about 1:1.2. The amount of organosulfonic acid II which is used should be in a molar ratio of from about 0.0001:1 to about 1:1, based on the amount of alkoxysilane II which is used. A preferred molar ratio is from about 0.0001:1 to about 0.1:1.

The three aforementioned reactants can be simultaneously charged into a suitable reaction vessel or, if desired, the water can be gradually added to a mixture of a sulfonic acid and alkoxysilane. Upon mixing an exothermic reaction results and it is generally desirable to heat the mixture to drive off by-product of the formula ROH, where R has the meaning given above. This heating can vary from about 80° C. to about 140° C. depending on the particular by-product produced by the reaction.

More preferably, the reaction is carried out in two stages, initially inducing a substantial amount of hydrolysis into a suitable alkoxysilane in the presence of organosulfonic acid and subsequently adding additional alkoxysilane followed by heating the reaction mixture to remove the by-product alkanol.

A third route to the polymeric alkoxysilanes I comprises first reacting the alkoxysilane II with the organosulfonic acid III in the absence of water to provide a monomer having the general formula

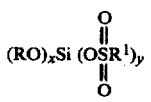

IV where R and $R^1$ are as previously described and x and y have values, the sum of which is 4 with y being less than 1. The addition of water to this monomer, followed by removal of the alkanol by-product by distillation, results in polymeric alkoxysilanes of the average general formula I.

The polymers produced according to this invention contain 20 to 70% and preferably 45–55%, by weight $SiO_2$, and generally the molecular weight distribution can be controlled by appropriate manipulation of reaction conditions. For example, the proportion of low molecular weight polymer can be substantially reduced by decreasing the amount of alkoxysilane added during the second step of the reaction sequence.

The polymeric alkoxysilanes I prepared in accordance with the invention are stable mixtures having excellent shelflife, since they cannot cure in the absence of moisture. When curing is desired, they ideally should be exposed to about 50% relative humidity. However, they have been found to cure within an hour at 10% and lower relative humidity, an excellent performance characteristic for such [storagestable] *storage stable* materials.

The polymeric alkoxysilanes I are useful in many areas. For example, they are suitable for use in formulating zinc-rich paints for the protection of ferrous surfaces. These paints generally contain from 5–15 percent by weight of the polymeric alkoxysilane I and from 95–85 percent by weight of powdered zinc. Other components, such as extenders, fillers and pigments can also be added in amounts up to 20 percent of the weight of the zinc.

Another valuable use for the polymeric alkoxysilanes I of this invention is in the preparation of molds for investment casting. These refractory molds are prepared by admixing comminuted refractory material with the polymeric alkoxysilane and sufficient solvent to obtain adequate viscosity to make the mold. Then a mold is formed by applying the resulting mixtures to a pattern and allowing it to set. Alternately, gelling agents can be added to accelerate curing. Suitable gelling agents are known in the art, and include ammonia, ammonium carbonate, etc. After setting, the mold is stripped from the pattern, dried and molten metal is poured into the mold. It will be appreciated that the presence of the alkoxy, alkoxyalkyl and aryloxy groups in the polymeric alkoxysilanes of this invention allows the compounds to break down into materials containing a substantial amount of silica upon firing, a highly desirable property for this application.

While all the polymeric alkoxysilanes I have excellent properties, particularly preferred are those compounds I where R is lower alkyl, i.e., alkyl of 1–4 carbon atoms, $R^1$ is lower alkyl, phenyl or alkylphenyl where the alkyl substituent is methyl or ethyl, a has a value from 1.2 to 2.4 and b has a value from 0.0001 to 0.1.

The following examples will serve to illustrate the practice of this invention. All parts are by weight unless otherwise specified.

EXAMPLE I

This example illustrates preparing methanesulfatotriethoxy silane.

In a 50 ml. flask equipped with a short path distillation head, ethyl silicate, condensed (containing about 95% by weight tetraethyl orthosilicate) ([20.3] *20.8* gram, 0.1 mole) and methanesulfonic acid (9.6 grams, 0.1 mole) were stirred at 100 mm Hg. After 30 minutes, the pressure was reduced to 10 mm Hg and the reaction mixture distilled.

The fraction boiling at 101°–105° C. (10 mm Hg) was collected. Infrared examination of the distillate showed no hydroxyl absorption between 3400 and 3600 $cm^{-1}$ and strong $SO_2$ absorption at 1350 $cm^{-1}$.

Nuclear magnetic resonance spectroscopy revealed the presence of terminal methyl protons appearing as a triplet at 1.25 δ confirming the presence of 9 protons; the presence of methanesulfonyl protons appearing as a singlet at 3.0 δ confirming the presence of 3 protons and the presence of methylene protons appearing as a quartet at 3.9 δ confirming the presence of 6 protons.

This data was consistent with a formula for the product of:

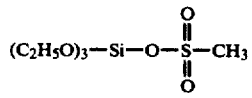

The liquid product was extremely moisture sensitive, rapidly hydrolyzing to a white powder on exposure to atmospheric water.

EXAMPLE 2

A. Preparation of Polymeric Alkoxysilane

In a 12 liter 3 necked reactor equipped with mechanical stirrer, addition funnel and Claisen head adapter with attached thermometer and Newman-type distillation head, ethyl silicate, [condensed] *40% $SiO_2$* (2976 grams) in 400 grams of ethanol was stirred under nitrogen. A solution of p-toluenesulfonic acid (72 grams), water (432 grams) and 100 grams of ethanol was added over an hour period such that the temperature rose to 50° C. and remained there. Toward the end of the addition, heating was begun to maintain the temperature. After completion of the addition, the reaction mixture was maintained at 50° C. for 1½ hours at which time ethylsilicate condensed (4160 grams) was added and the mixture allowed to stand overnight at ambient temperature. The reaction mixture was heated to remove by-product and solvent ethanol, distillation beginning at 80° C. After 3 hours the reaction mixture had reached 110° C. and the distillation has substantially slowed. After an additional 2 hours at 110° C. the product was cooled and bottled under nitrogen. The yield was 5.26 kilograms while 2.7 kilograms of ethanol were removed. The clear yellow liquid analyzed for 44.0% $SiO_2$ (theory for product [43.8] *44.2%*) whose calculated formula is $$[\,Si(OC_2H_5)_{1.981}(O\overset{O}{\overset{\|}{S}}-C_7H_7)_{0.019}O\,]$$

$$Si(OC_2H_5)_2\,(O\overset{O}{\overset{\|}{S}}-C_7H_7)_{0.009}O$$

The shelflife of this material at 65° C. is greater than 1 year as compared to [one month] *six months* for commercial binder Silbond H-4, a prehydrolyzed ethylsilicate binder available from Stauffer Chemical Company, Westport, Conn.

B. Preparation of Slurry

The sample prepared in part A above was diluted to 10.0% $SiO_2$ content with denatured ethanol to provide Binder A and compared to the commercial binder Silbond H-4 in the following slurry formulation:

4.00 parts Binder
9.85 parts Refractory.

The refractory comprised 1.0 part by weight of -200 mesh milled zircon, available from M and T Company, Rahway, N.J., and 3.5 parts Rancosil-120 mesh fused silica, available from Ramson and Randolph Co., Toledo, Ohio.

Binder A performed satisfactorily in all aspects of mold-making.

C. Preparation of Paint

The sample as prepared in part A above was diluted to 18% $SiO_2$ with 95% ethoxyethanol to provide Binder B and formulated into and following zinc rich paint.

| | |
|---|---|
| Binder B | 24.1 parts |
| Celite 499[1] | 2.1 |
| Bentone 27[2] | 0.3 |
| Zinc | 73.5 |

[1]Celite 499 is a diatomaceous silica available from Johns Manville Corp., Denver, Colorado.
[2]Bentone 27 is an organic modified clay available from N. L. Industries, Heights Town, N.J.

A similar formulation was prepared but using Silbond H-6 instead of Binder B. Both paints were brush applied to sand-blasted steel test panels and dried to a 3 mil thickness. The standard Pencil Test was used to determine hardness. Solvent resistance was determined by wiping the coating with a rag saturated with methyl ethyl ketone. Pot life represents the time prior to gellation. The results are set forth in the table.

| | SILBOND H-6 | Binder B |
|---|---|---|
| Hardness (30 min) | less than 6B | 6B |
| Solvent (resistance) | good-fair | good |
| Pot Life (hr) | 32 | greater than 45 |

EXAMPLE 3

A. Preparation of Polymeric Alkoxysilane

This reaction was carried out employing the ingredients and the essentially identical method described in Example 2 except that the amount of ethyl silicate, condensed added in the second step was only 2080 grams. The product of this reaction was stripped until it contained 50% $SiO_2$ as determined by the amount of ethanol removed. Analysis of the isolated product revealed the pale yellow liquid to contain approximately 50.1% $SiO_2$ (average of two determinations). The product, which was obtained as a 91% by weight solution in ethanol, had the following calculated formula:

$$[Si(OC_2H_5)_{1.3}(OSO_2C_7H_7)_{0.02}O_{13}]$$

$$Si(OC_2H_5)_{1.3}(OSO_2C_7H_7)_{.012}O_{1.3}$$

B. Preparation of Mold

The binder prepared in part A was mixed with Rancosil-120 mesh fused silica in a weight ratio of 4.00 parts binder to 9.85 parts fused silica.

A wax pattern was precoated by dipping in a slurry of 325 mesh fused silica in colloidal silica, drying, dipping again and drying overnight. Then the pattern was dipped in the slurry of Rancosil-120 mesh and binder. Immediately thereafter, the pattern was immersed in a fluidized bed of 60-80 mesh fused silica, to promote adhesion of subsequent coats. The procedure was continued with alternate dippings in the slurry and fluidized bed until the pattern had been dipped in the slurry six times and the fluidized bed five times. The entire process required only 1 hour and 10 minutes, representing a significant increase in rate of cure when contrasted with a similar slurry using the previously described Silbond H-4 as the binder.

EXAMPLE 4

A preparation for forming a polymer comprising a moiety derived from an alkyl ether of ethylene glycol is shown herein.

Ethyl silicate, condensed (4 moles) and toluene sulfonic acid (20 grams) were combined in a three neck, two liter flask equipped with a distillation head, stirrer and addition funnel. Water (4.8 moles) in ethylene glycol monethyl ether (5.56 moles), available as "Ethyl Cellosolve" from Union Carbide Corporation, were added to the ethyl silicate, condensed over the space of 1 hour. The temperature rose from about 24° C. to about 41° C., and the mixture was rapidly brought to reflux.

As the mixture refluxed, its color changed from light yellow to white. Over the next 2½ hours ethanol (756 grams) was removed as the temperature was raised from 88° C. to 140° C., at which temperature the distillation of ethanol ceased. The color of the solution at this point was dark brown, and it was heated for 15 minutes at 140° C. under nitrogen and was then cooled to room temperature. The product weighed 559 grams.

The product cured to a solid upon exposure to air (30% relative humidity) for 20 minutes. The product was soluble in water if the water was slowly added to it. Addition of the product to water resulted in formation of an emulsion.

What is claimed is:

1. A polymeric alkoxysilane having the average formula $$Si(OR)_a(O-\overset{\overset{O}{\|}}{\underset{\underset{O}{\|}}{S}}-R^1)_bO_{\frac{4-a-b}{2}}$$

wherein each R is an independently selected hydrocarbon radical or hydrocarbon ether radical free of aliphatic unsaturation, each $R^1$ is an independently selected hydrocarbon radical free of aliphatic unsaturation, a has a value from 1 to 3 and b has a value from [0.001] *0.0001* to 1.0.

2. The polymeric silane of claim 1 where each R is an independently selected alkyl or alkoxyalkyl of 1 to 18 carbon atoms, aryl of 6 to 13 ring carbon atoms or alkylsubstituted aryl where the aryl has 6 to 13 ring carbon atoms and the alkyl from 1 to 5 carbon atoms, and each $R^1$ is an independently selected alkyl of 1 to 18 carbon atoms, aryl of 6 to 13 ring carbon atoms or alkylsubstituted aryl where the aryl has from 6 to 13 ring carbon atoms and the alkyl from 1 to 5 carbon atoms.

3. The polymeric alkoxysilane of claim 1 wherein R is lower alkyl; [R'] $R^1$ is lower alkyl, phenyl or alkylphenyl where the alkyl group has 1 or 2 carbon atoms; a is an integer from 1.2 to 2.4 and b is an integer from 0.001 to 0.1.

4. The [polymeric] alkoxysilane of claim 2 having the formula $$(C_2H_5O)_3-Si-O-\overset{\overset{O}{\|}}{\underset{\underset{O}{\|}}{S}}-CH_3.$$

5. The polymeric alkoxysilane of claim 3 having the formula $$[(C_2H_5O)_{1.981}-Si-(O-\overset{\overset{O}{\|}}{\underset{\underset{O}{\|}}{S}}-C_6H_4CH_3)_{0.019}.]$$

$$Si(OC_2H_5)_2(O\overset{\overset{O}{\|}}{\underset{\underset{O}{\|}}{S}}-C_7H_7)_{0.009}O$$

6. The polymeric alkoxysilane of claim 3 having the formula $$[Si(OC_2H_5)_{1.3}(O-\overset{\overset{O}{\|}}{\underset{\underset{O}{\|}}{S}}-C_7H_7)_{0.01}O_{1.13}.]$$

$$Si(OC_2H_5)_{1.3}(O-\overset{\overset{O}{\|}}{\underset{\underset{O}{\|}}{S}}-C_7H_7)_{.012}O_{1.3}$$

* * * * *